(12) United States Patent
Tonks et al.

(10) Patent No.: US 8,839,794 B2
(45) Date of Patent: Sep. 23, 2014

(54) DISPOSABLE APPARATUS FOR SECURING A PATIENT

(76) Inventors: Cheri J. Tonks, Herriman, UT (US); Russell Tonks, Herriman, UT (US)

(*) Notice: Subject to any disclaimer, the term of this patent is extended or adjusted under 35 U.S.C. 154(b) by 46 days.

(21) Appl. No.: 13/439,781

(22) Filed: Apr. 4, 2012

(65) Prior Publication Data
US 2012/0247488 A1 Oct. 4, 2012

Related U.S. Application Data

(60) Provisional application No. 61/471,639, filed on Apr. 4, 2011.

(51) Int. Cl.
*A61F 5/37* (2006.01)
*A61B 19/08* (2006.01)

(52) U.S. Cl.
CPC . *A61B 19/08* (2013.01); *A61F 5/37* (2013.01); *A61B 2019/085* (2013.01); *A61B 19/088* (2013.01); *A61F 5/3776* (2013.01)
USPC ............ 128/849; 128/854; 128/869; 128/870

(58) Field of Classification Search
USPC ................. 128/849, 854, 869, 870, 872–876; 224/158; 150/154
See application file for complete search history.

(56) References Cited

U.S. PATENT DOCUMENTS 6,227,201 B1* 5/2001 Ferko, III ...................... 128/869
7,707,667 B1* 5/2010 Walton ............................. 5/626

OTHER PUBLICATIONS

"Olympic Papoose Boards" Natus, available at: http://www.natus.com/index.cfm?page=products_1&crid=109&contentid=202, 2 pages, last accessed Apr. 4, 2012.

* cited by examiner

*Primary Examiner* — Patricia Bianco
*Assistant Examiner* — Keri J Nelson
(74) *Attorney, Agent, or Firm* — Jeffery T. Holman

(57) ABSTRACT

Embodiments of an apparatus are described. In one embodiment, the system is an apparatus for securing a patient to a board. The apparatus includes a board and a disposable cover that covers at least a portion of the board. The disposable cover includes a securing mechanism for securing the cover in place around a portion of the board. The disposable cover further includes at least one strap to wrap around the body of a patient or other object. The disposable cover also includes at least one second strap to wrap around the first strap. The second strap may include an adhesive material to secure the second strap around the first strap.

14 Claims, 2 Drawing Sheets

DISPOSABLE APPARATUS FOR SECURING A PATIENT

CROSS-REFERENCE TO RELATED APPLICATIONS

This application claims the benefit of priority of U.S. Provisional Patent Application No. 61/471,639, entitled "Disposable Apparatus for Securing Patient" filed Apr. 4, 2011, which is incorporated herein in its entirety.

BACKGROUND

In some medical applications, it can be beneficial to use a restraint system to immobilize a patient. Immobilization may be useful to prevent unwanted movement of a patient during transport and/or surgery. Immobilization may be especially useful when providing medical services to combative or frightened patients for whom it may be difficult to relax and remain calm.

One conventional type of restraint system uses a rigid board with multiple securing straps. In some conventional device, the securing straps are wide bands of material that are detachable (e.g., using VELCRO) from the rigid board. The patient is secured to the rigid board using the straps, which may be individually secured around the patient's body and extremities. The individual nature of the straps can also facilitate selective access to specific areas of the patient's body by medical personnel.

In order to provide some level of comfort to the patient, the rigid board may have a padded surface that is permanently secured to at least one side of the rigid board. This padded surface provides a more comfortable surface for the patient's back and allows for some cushioning as the straps are tightened around the patient.

Unfortunately, conventional restraint systems with integrated padding are difficult to maintain clean and sanitary. Patients in need of medical attention can soil the restraint system with blood or other bodily fluids, which can be difficult to effectively remove from seams or zippers in the padded covering and/or seams between the covering and the supportive board. While it may be possible to sanitize the board's surfaces to an acceptable degree, it can be difficult to fully clean the board in some instances. In some situations, nurses simply remove the removable straps and wipe down the board and padding with a cleaning agent. The removable straps may be laundered separately (e.g., at another location such as a laundry facility of a hospital). Additionally, the cleaning process typically involves taking the board out of use for some time while the straps are sent for cleaning. In a medical environment where there are typically few boards available for a given department or facility, sending the board out for thorough cleaning means that the board is not available for medical use during that time. The cleaning process can also be made difficult because the typical hook and loop material used to secure the straps together often retain foreign materials that are difficult to fully remove, thus negatively affecting the securing properties of the straps.

SUMMARY

Embodiments of an apparatus herein relate to a disposable apparatus for restraining a medical patient to a board. In one embodiment, the apparatus includes a board and a disposable cover that covers at least a portion of the board. The disposable cover includes a securing mechanism for securing the cover in place around a portion of the board. The disposable cover further includes at least one strap to wrap around the body of a patient or other object. Further, the disposable cover includes at least one strap to wrap around the first strap. The second strap may include an adhesive material to secure the second strap around the first strap.

In some embodiments, the disposable cover defines an interior pocket of a size and a shape suitable to receive the board within the disposable cover. The disposable cover may further include a flap with an adhesive material. The flap is configured to fold over an opening used to access the interior pocket of the disposable cover to secure the board within the disposable cover.

In some embodiments, the board includes at least one slotted opening at a peripheral edge of the board, and the disposable cover is configured to secure to the board by passing through the slotted opening prior to wrapping around a patient. The board may include a plurality of slotted openings, with at least two slotted openings along a first side edge of the board and at least two additional slotted openings along a second side edge of the board. In this example, the disposable cover includes corresponding straps to align with the plurality of slotted openings along each side edge of the board.

In some embodiments, the disposable cover is fabricated from a medical drape material. The medical drape material includes a barrier layer to prevent liquid from passing through the medical drape material. The barrier layer also may prevent bacteria from passing through the medical drape material. Other embodiments may use other types of commonly disposable materials with the same or different characteristics.

In some embodiments, the adhesive material includes an adhesive tape, which adheres to at least one of the straps and is configured to adhere to the other corresponding strap upon application of the adhesive material to the other strap to secure the patient to the board with the pair of straps. In an alternative embodiment, the adhesive material includes a hook-and-loop material such as VELCRO. In this example, a hook layer portion of the hook-and-loop material is secured to one strap, and a corresponding loop layer portion of the hook-and-loop material is secured to another corresponding strap, so that the hook layer portion and the loop layer portion can adhere together upon contact when the first and second straps are wrapped together.

Other embodiments of the system are also described. Other aspects and advantages of embodiments of the present invention will become apparent from the following detailed description, taken in conjunction with the accompanying drawings, illustrated by way of example of the principles of the invention.

BRIEF DESCRIPTION OF THE DRAWINGS

Throughout the description, similar reference numbers may be used to identify similar elements.

DETAILED DESCRIPTION

Figure 1:
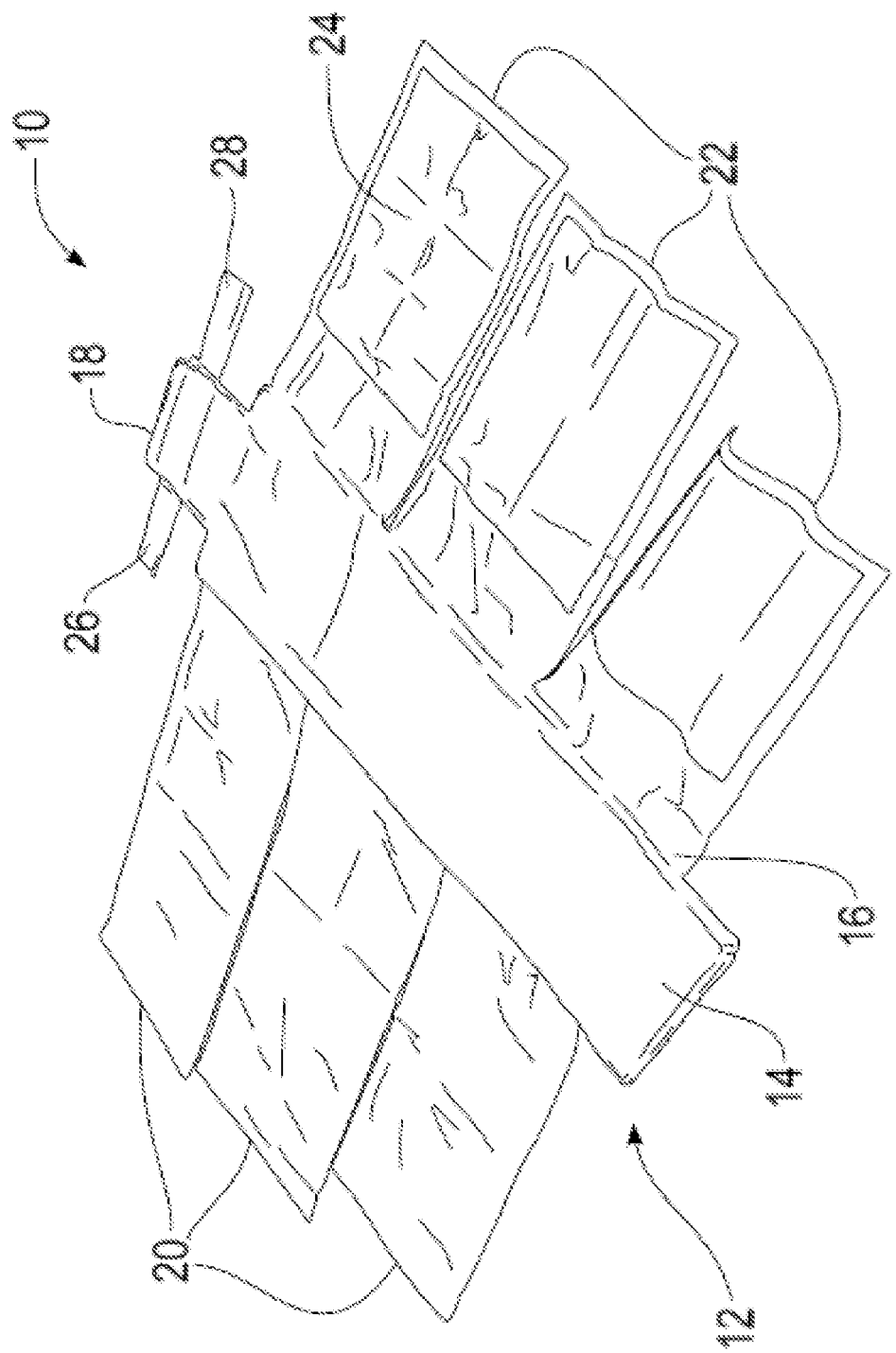
FIG. 1 depicts a diagram of one embodiment of an apparatus for securing a patient to a board in an open position.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

While many embodiments are described herein, at least some of the described embodiments include a disposable securing mechanism. The disposable securing mechanism can be used in conjunction with a conventional rigid board, which may or may not have padding to cushion the patient. In some embodiments, the disposable securing mechanism is a cover that is placed over and secured to the rigid board so that the board is protected against common soiling agents that might be present during medical transport and patient care procedures.

The cover is made from a material that is accepted in the medical field as being disposable. Examples of disposable material include any medical drape material that is commonly available for single-use applications.

In this description, a securing mechanism may refer to any object or mechanism for securing a cover to a board or for securing straps together in a tight or secure position. Moreover, while many embodiments describe a board for holding a patient, the board may refer generally to any surface, portable or stationary, upon which a patient may lie and be held in a secure position.

FIG. 1 discloses a diagram of one embodiment of an apparatus 10 for securing a patient to a board 12. The apparatus 10 includes a board 12 and a cover 16 that fits around and covers at least a portion of the board 12. The illustrated board 12 includes a body portion 14 and a head portion 18 corresponding to the placement of the head and body of a patient. The board 12, however, may be any shape that is capable of holding a patient or other object, such as a coffin shape or a V-shape, as well as a uniform width across the length of the board 12. The board 12 may be any conventional board used for the transportation of persons or objects, either for medical, emergency, or other transportation purposes, and need not specifically conform to the shape or size of the illustrated embodiment.

The board 12 may be made of a variety of materials, including metals, plastics, or other durable materials capable of holding the weight of a person or other object. Also, the board 12 may be portable, such as those used by ambulances and other emergency medical units or those used within hospitals to transport patients between different locations of a hospital. Furthermore, the board 12 may be a stationary fixture, or attached to a stationary fixture, such as an operating table, hospital bed, or other object where a patient could sit or lie.

Additionally, to enhance the comfort of a patient, the board 12 may include a cushion or padding on the surface of the board 12. The board 12 may be washed between uses, and the cushion or padding may be fixed or removable for replacement, sanitation, washing or other purposes.

In some embodiments, the board 12 also may include slots, indentations, or other mechanical features that can be used as grips as the board is manipulated by personnel. Such slots, indentations, or other mechanical features also may be used, in some instances for securing at least a portion of the cover 16 to the board 12. For example, in some embodiments a portion of the cover 16 may pass through a slotted opening in the board 12 in order to secure the cover 16 to the board 12.

The illustrated apparatus 10 further discloses a cover 16 that may slide around or attach to the board 12. The cover 16 may be made from a variety of materials that are durable and capable of securing a patient to a board 12. By way of example, the cover 16 may be made from a surgical drape material, or any material that is strong and relatively inexpensive for disposal and replacement purposes.

The board 12 may be placed into the cover 16, for example, at an opening at one end of the cover 16, or through an opening on the top or bottom surface of the cover 16. The cover 16 may also include a securing mechanism for securing the cover to the board 12. The securing mechanism may include an adhesive material to close the opening once the board 12 is in the cover 16. In other embodiments, other types of securing mechanisms such as clips, zippers, adhesive materials, ties, cords, fastening points, may be used for securing the cover 16 in place around the board 12. Additionally, in some embodiments, the cover 16 may be secured to the board by stretching the material of the cover 16 over the board 12 to create a tight fit that stays in place when a patient is placed on the board 12. In an alternative embodiment, the cover 16 may be threaded through one or more openings in the sides of a board 12 and wrapped around the patient. These openings may be used to carry the board 12, as well as for wrapping additional material around the individual arms and/or legs of the patient.

The apparatus 10 further includes a plurality of straps 20, 22 extending from each side of the board cover 16. Specifically, the illustrated embodiment discloses three longer straps 20 on one side of the board 12 that may wrap around a patient on the board 12. The straps 20 may cover a portion or the entire patient depending on the size of the patient and length of the straps 20. Also, the straps 20 may be designed to wrap around the entire body of the patient and tucked around the body to create a tight fit around the body of the patient. The straps 20 may also be cut or otherwise adjusted in length in order for the apparatus 10 to conform to different sizes of patients. Furthermore, while the illustrated embodiment discloses three longer straps 20, the board cover 16 may include more or less straps of varied lengths, and need not conform to the specific design features of the illustrated embodiment.

The illustrated cover 16 further includes a plurality of shorter straps 22 on the opposing side of the cover 16 from the longer straps 20. The shorter straps 22 may wrap around the body of a patient and fasten to the longer straps 20 to secure the patient in a fixed position relative to the board 12. As illustrated, the straps 22 may have adhesion elements 24 for fastening the surface of the shorter straps 22 to the longer straps 20. When attached, the shorter straps 22 attach to the longer straps 20 wrapped around the patient creating a tight fit around the body of a patient and securing the patient in a fixed position relative to the board 12. While the illustrated embodiment includes shorter straps 22 and longer straps 20, the length of the straps 22 may in fact be longer than the straps 20, or they may be equal in length, regardless of the specific design of the illustrated embodiment. Additionally, while the illustrated embodiment only discloses adhesive material 24 on the shorter straps 22, either strap 20, 22 within a given pair of straps may utilize adhesive material. Or both straps 20, 22 within a given pair of straps may have adhesive material attached thereto. Some examples of adhesive material include, but are not limited to, adhesive tape (available from 3M) or a hook and loop mechanism such as VELCRO. Furthermore, the adhesive material may be used to secure the straps 20, 22 together or alternatively to secure the straps directly to a patient on the board 12.

The illustrated cover 16 further includes two head straps 26, 28 on opposing sides of the board cover 16. When a patient is secured by the straps 20, 22, the head straps 26, 28 may wrap around the head of a patient, thereby locking the head into a secure position. The head straps 26, 28 may include adhesive material that attaches directly to the patient, specifically to lock their head into place. This prevents the movement of the patient's head, and prevents further injury that may take place in the transportation of a patient. Optionally, the head straps 26, 28 may be used in conjunction with a device to immobilize the patient's neck, too. Although the illustrated embodiment discloses two head straps 26, 28, the board cover 16 may only include a single head strap of varying lengths and width. Additionally, a head strap 26 may be long enough to wrap around the entire head of a patient, once or multiple times, and perform the similar function of securing a patient into a still position.

Although the illustrated embodiment includes a specific number of straps, other embodiments may include fewer or more straps, different sizes of straps, or different placements of the straps. For example, one or more additional straps may be provided to individually secure a patient's leg or arm. In another embodiment, one or more straps may be used to secure around the board 12, in addition to the straps used to secure the patient.

In at least one embodiment of the apparatus 10 for securing patients to a board 12, the board cover 16 is disposable. After the cover 16 has been used on a specific patient, the cover 16 may be removed from the board 12 and discarded.

Figure 2:
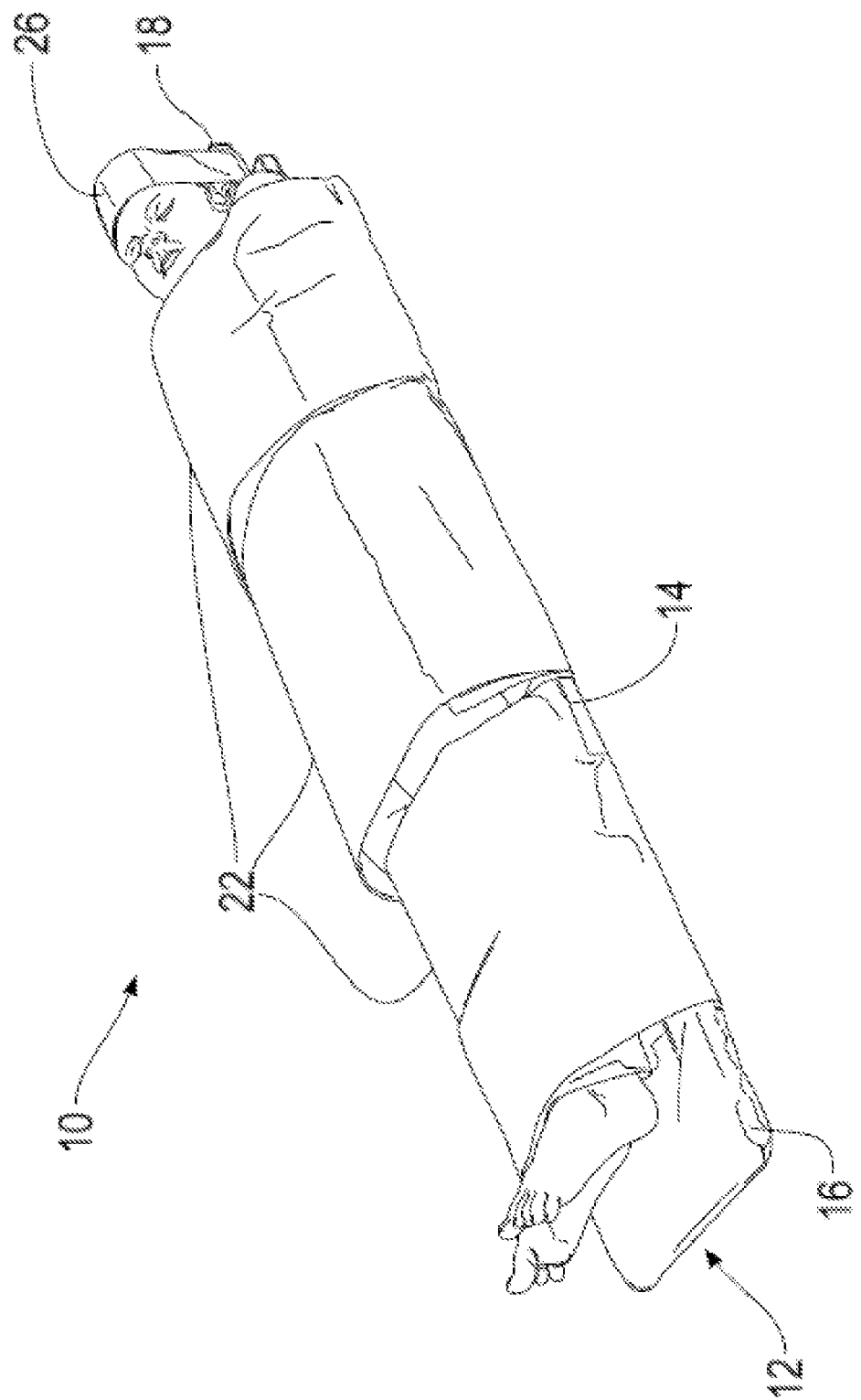
FIG. 2 depicts a diagram of one embodiment of an apparatus for securing a patient to a board in a closed position.

FIG. 2 depicts a diagram of one embodiment of an apparatus 10 for securing a patient to a board 12. In the illustrated embodiment, the apparatus 10 includes a board 12 including a body portion 14, a head portion 18, and a cover 16 similar to other embodiments described herein. The apparatus 10 for securing a patient is in a closed position, wherein the straps 22 of the board cover 16 are secured around a patient to hold the patient in a fixed and secure position. The illustrated embodiment further discloses the head strap 26 in a closed position, wherein the head strap 26 is wrapped around and secured to the head of a patient, holding the patient's head in a secure position. While the illustrated embodiment shows a patient secured to a moveable board 12, the board 12 may be any other fixture, portable or stationary, that may be used to hold a patient in place for securing the body in a fixed or secure position.

One advantage of several embodiments is the disposable nature of the cover 16. Medical patients generally prefer to use products that have been previously unused by other patients, such as disposable robes, needles, gloves, etc. The disposable nature of the cover 16 meets this preference, as well as providing a sanitary and convenient way to facilitate the transition between different patients that use the same board 12. Additionally, washing and/or reusing covers is costly and time-intensive and often presents difficulties in the degrading quality of the material due to wear and tear or the inability to adequately clean blood, fluids, or other substances that may come into contact with the cover and any related seams or zippers. Furthermore, the disposable cover 16 is made of a durable, inexpensive material that protects the board 12, and increases the amount of time before a board 12 must be replaced after extensive or repetitive use and cleaning.

Another advantage that may be achieved by use of disposable cover 16 is maintaining the board 12 available for immediate reuse as soon as each previous disposable cover 16 is removed and a new cover is installed.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. An apparatus for securing a patient to a board, the apparatus comprising:
    a disposable cover that covers at least a portion of a board, wherein the disposable cover covers an anterior side and a posterior side of the board, the disposable cover comprising:
        a securing mechanism for securing the cover in place around the portion of the board;
        a plurality of first straps to wrap around the body of the patient, wherein the first straps are located on a first side of the disposable cover; and
        a plurality of second straps to wrap around the plurality of first straps, wherein the second straps are located on a second side of the disposable cover, wherein the second side is opposite the first side, wherein the plurality of second straps comprises an adhesive material to secure the plurality of second straps to the plurality of first straps, wherein the plurality of first straps and the plurality of second straps and the disposable cover are a same material, and wherein the plurality of first straps is configured to cover a majority of a torso and legs of the patient.

2. The apparatus of claim 1, wherein the disposable cover defines an interior pocket of a size and a shape suitable to receive the board within the disposable cover.

3. The apparatus of claim 1, wherein the disposable cover is fabricated from a medical drape material.

4. The apparatus of claim 3, wherein the medical drape material comprises a barrier layer to prevent liquid from passing through the medical drape material.

5. The apparatus of claim 4, wherein the barrier layer is further configured to prevent bacteria from passing through the medical drape material.

6. The apparatus of claim 1, wherein the adhesive material comprises an adhesive tape, which adheres on a first side to the plurality of second straps and is configured to adhere on a second side to the plurality of first straps upon application of the adhesive material to the plurality of first straps.

7. The apparatus of claim 1, wherein the adhesive material comprises a hook layer portion of a hook-and-loop material, and a corresponding loop layer portion of the hook-and-loop material is secured to the plurality of first straps, wherein the hook layer portion and the loop layer portion are configured to adhere together upon contact when the plurality of first and second straps are wrapped together.

8. A disposable cover for a patient board, the disposable cover comprising:
a securing mechanism for securing the cover in place around at least a portion of the board;
a plurality of strap pairs made of medical drape material, wherein each strap pair comprises first and second straps to wrap around a body of a patient when the patient is positioned on the cover and the board, wherein the plurality of straps pairs are configured to cover a majority of a torso and legs of the patient; and
an adhesive material coupled to at least one of the first and second straps within each strap pair, wherein the adhesive material is configured to adhere the corresponding first and second straps together to secure the body of the patient to the board.

9. The disposable cover of claim 8, wherein the disposable cover defines an interior pocket of a size and a shape suitable to receive the board within the disposable cover.

10. The disposable cover of claim 8, wherein the medical drape material comprises a barrier layer to prevent liquid from passing through the medical drape material.

11. The disposable cover of claim 8, wherein the medical drape material comprises a barrier layer to prevent bacteria from passing through the medical drape material.

12. The disposable cover of claim 8, wherein the adhesive material comprises an adhesive tape, which adheres on a first side to one of the straps within a strap pair and is configured to adhere on a second side to the other corresponding strap within the strap pair upon wrapping the straps around the patient.

13. The disposable cover of claim 8, wherein the adhesive material comprises a hook layer portion of a hook-and-loop material, and a corresponding loop layer portion of the hook-and-loop material is secured to one of the straps within a strap pair, wherein the hook layer portion and the loop layer portion are configured to adhere together upon contact when the straps of the strap pair are wrapped together.

14. The disposable cover of claim 8, further comprising at least one additional strap pair, wherein the additional strap pair comprises first and second straps to wrap around an underside of the board to at least partially secure the disposable cover to the board.

\* \* \* \* \*